(12) United States Patent
Gange

(10) Patent No.: US 6,271,175 B1
(45) Date of Patent: Aug. 7, 2001

(54) GRASS TREATMENT

(75) Inventor: Alan C. Gange, Egham (GB)

(73) Assignee: The MicroBio Group Limited, Cambridge (GB)

( * ) Notice: Subject to any disclaimer, the term of this patent is extended or adjusted under 35 U.S.C. 154(b) by 0 days.

(21) Appl. No.: 09/600,687

(22) PCT Filed: Jan. 19, 1999

(86) PCT No.: PCT/GB99/00167
§ 371 Date: Sep. 11, 2000
§ 102(e) Date: Sep. 11, 2000

(87) PCT Pub. No.: WO99/37156
PCT Pub. Date: Jul. 29, 1999

(30) Foreign Application Priority Data

Jan. 22, 1998 (GB) .................................................. 9801370

(51) Int. Cl.$^7$ .................................................. A01N 63/04
(52) U.S. Cl. .................................................. 504/117
(58) Field of Search .................................................. 504/117

(56) References Cited

U.S. PATENT DOCUMENTS 5,559,079 * 9/1996 Imaizumi et al. .................... 504/117

FOREIGN PATENT DOCUMENTS 0 661 001 * 7/1995 (EP) .
1 437 877 * 6/1976 (GB) .
95/12980 * 5/1995 (WO) .

OTHER PUBLICATIONS

JPOABS Abstract of JP 04–166018, Jun. 1992.*
Gemma et al. "Mycorrhizal fungi improve drought resistance in creeping bentgrass" J. Turfgrass Science. 73:15–29, 1997.*
Gemma et al. "Enhanced establishment of bentgrasses by arguscular mycorrhizal fungi" J. Turfgrass Science. 73:9–13, 1997.*
Allen, Michael F., et al., Responses on the non–mycotrophic plant *Salsola kali* to invasion by vesicular–arbuscular mycorrhizal fungi, *New Phytology* (1989), 11, 45–49.
Plant Health Care Inc. Data Sheet #26, Mycor™ Turf Saver™ (2 pages), Jul. 1997.

* cited by examiner

Primary Examiner—S. Mark Clardy
(74) Attorney, Agent, or Firm—Craig A. Fieschko, Esq.; DeWitt Ross & Stevens S.C.

(57) ABSTRACT

A mycorrhiza have growth-retardant activity for *Poa annua* and may be used to control the growth of *P. annua* in high quality sport or amenity turf consisting mainly of Agrostis or Festuca species. Strains of VA mycorrhiza selected from genera Glomus, Acaulospora, Entrophosphora, Gigaspora, Scutellospora and Scierocytis may be used. The VA mycorrhiza is applied to the soil as a formulated product in which the VA mycorrhizae constitute the principal component having biological activity on the growth of turf grass. Dose rates of inoculum having an MPN of from about 200 To 1000 or more propagules per gram are effective and may be formulated with a clay or other solid carrier. The amount of formulated product applied to the turf may be from about 5 $g/m^2$ to about 1 $kg/m^2$. The infective prop are selected from fungal spores, mycelium, hyphae, and fragments of mycorrhiza infected roots. These may be applied to sport or amenity turf, or other grassy area in need of *P. annua* control, or an area in which high quality turf-grass is to be laid or sown.

19 Claims, 8 Drawing Sheets

GRASS TREATMENT

This invention relates to methods and compositions for improving the quality of turf grass. More particularly, the invention is concerned with the control, reduction, or elimination of undesirable grass components of turf, especially of high quality turf consisting mainly of Bentgrass such as *Agrostis stolonifera* or Festuca species.

Poa annua or Annual Meadow grass (AMG) (also called Annual Bluegrass) is the most troublesome weed of bent grass putting greens in countries as diverse as the United Kingdom, the United States of America, and Australia. *P. annua* is generally considered to be undesirable in putting greens because it is susceptible to abiotic stress, particularly water availability, as well as succumbing to a number of fungal diseases. In addition, if a green is composed of patches of AMG and bent grass, the surface is not as uniform as many players would wish it to be.

Some turf managers attempt to control *P. annua*. The most widely used control method is herbicide application, and a number of compounds have been tested against the species with varying success. However, application of pesticides can be costly, and they may present a problem of groundwater pollution if the green is well irrigated. In addition, there may be associated health risks to golfers or greens staff. Therefore, if AMG is to be controlled on putting greens, a more natural, environmental approach is called for.

The present inventor has previously reported that the abundance of AMG in a golf green may be negatively related to the abundance of fungi in the soil (Gange A. C. 1994, Subterranean insects and fungi: hidden costs and benefits to the greenkeeper. In Science & Golf II, Proceedings of the World Scientific Congress of Golf, eds. A. J.Cochran and M. R. Farrally, 461–466, London E. and F. N. Spoon ). The fungi concerned were vesicular-arbuscular mycorrhizas which are generally abundant in natural plant communities. It was found that the fungi were very low in abundance in golf turf, but when they were common in the soil, there was less AMG in the sward, and vice versa. The original explanation for this relation was that as bentgrass is considerably more strongly mycorrhizal than AMG, then in greens where fungal abundance is high, the bentgrass is more vigorous, and therefore is able to out-compete the AMG.

It has now been found that VA mycorrhizae have a direct growth-controlling effect on *Poa annua* and therefore provide an effective means of control of *P. annua* in turf grass consisting of high proportions of Bentgrass, or Festuca species. This is an unexpected finding for two reasons. First, *P. annua* is usually stated in the literature to be non-mycorrhizal or at most weakly mycorrhizal. Secondly, whilst it has now been found that VA mycorrhizae do colonise *Poa annua* roots, the colonisation retards rather than encourages growth. Moreover, this effect has been found to be independent of phosphorus levels in the soil.

The present invention is therefore based on the discovery of a novel technical effect of VA mycorrhizae which leads to a method of treatment of turfgrass which has not been contemplated hitherto. It is to be understood that the application of VA mycorrhizae, either to grassland or soil in preparation for grass sowing, in accordance with this invention is for the specific intention of suppressing *Poa annua*, as distinct from any other purpose e.g. to stimulate growth or for the recovery of damaged turf. Preparations for use according to the invention do not require the presence of any other bacteria or other organisms or biologically active materials, although these are not excluded if desired as incidental to the primary purpose of the invention.

It is especially important that the composition applied to turf contains very little of, and is preferably substantially free of, other biological materials which could promote growth of *P.annua* and therefore compete with the VA mycorrhiza and conflict with the objectives of the present invention. For example, because *P. annua* dominates turf in areas of high phosphate application, it is highly desirable to avoid the presence in the composition of significant amounts of bacteria which release P from phosphate. The deliberate addition of such phosphate-solubilizing bacteria to the composition is strongly contra-indicated. Preferably, therefore, apart from minimal amounts of other organisms which may be present due to the use of conditions of production which are not totally sterile, the VA mycorrhiza fungi used constitute the sole or principal organismic component of the compositions of the present invention.

The present invention comprises the use of a VA mycorrhiza as a growth-retardant for *Poa annua*. The term 'VA mycorrhiza' is used herein to cover all soil-borne fungi which form arbuscules in obligate mutualistic associations with terrestrial plants. Typical representatives of the vesicular-arbuscular fungi are found among the genera Glomus, Acaulospora, Entrophosphora, Gigaspora, Scutellospora and Sclerocytis. Exemplary strains are *Glomus fasciculatum, Glomus caledonium, Glomus mosseae, Glomus versiforme, Glomus intraradices,* and *Glomus etunicatum.* One or more strains of VA mycorrhiza may be used depending on the quality of the turfgrass to be treated. Preferred strains are those of *Glomus mosseae, caledonium, fasciculatum,* and *versiforme*. VA mycorrhizae are widely available organisms and may be obtained, for example, from the International Culture Collection of VAM fungi (INVAM), Florida, United States of America.

To produce VA mycorrhizal inoculum for the purposes of the present invention all infective structures of the fungus can be used, including spores and mycelium produced inside or outside the host root. Infected roots and infected substrates can also be used. Inoculum can be used in the form of slurries, gels, pellets, infected soil, or spore formulations. Especially effective formulations are the clay carrier-based formulations containing the four preferred strains indicated above e.g. those available commercially under the Registered Trade Mark 'VAMINOC' (The MicroBio Group Ltd, Whittlesford, Cambridge. UK), such as VAMINOC 8/16, VAMINOC 30/60, AND VAMINOC-T. Inoculant particle sizes can be up to 2 mm or 4–8 mm. Alternative carriers can be selected from, for example, silica gel, bleaching earths, pumice, bauxite, attapulgite, vermiculite, calcined montmorillinite, soil, peat, sand or any other substantially chemically inert material with a suitable porous structure.

The grass which may be treated according to the present invention may be a sport or amenity turf which is already established and which contains unacceptable proportions of *P. annua*. Turf which is mown regularly is particularly suitable for treatment. Alternatively the treatment may be applied to ground on which turf is to be laid or sown e.g. a sand/peat based green sown with bentgrass or a bentgrass/ Festuca mixture.

Desirably, the inoculum infectivity, as measured by the "most probable number" (MPN) technique, corresponds to MPN values of from at least 200 or 500 up to 1000 propagules or more per gram. Application of inoculum at a rate of at least 5 or 10 $g/m^2$ is effective but higher dosages may be used if preferred, e.g. up to about 100 to 250 $g/m^2$. Even higher doses, for example up to and in excess of 1 $Kg/m^2$, are envisaged in certain applications. The inoculum can be watered into an established green or introduced into the root zone. Application in weather which is either very warm or very cold is inadvisable. The turfgrass may be a golf green, a bowling green, a lawn, or any other kind of grassy area requiring treatment according to the invention. The invention is of particular importance in improving or maintaining the quality of turf consisting mainly of Agrostis Spp or Festuca Spp.

The invention also comprises a method of controlling or reducing the amount of *P. annua* in turfgrass which comprises applying to the turfgrass a growth-inhibiting strain of VA mycorrhiza. Preferably, a composition containing infective propagules is applied to the turfgrass, the composition containing propagules in sufficient quantities to effectively colonise plant roots. Infective propagules can be selected from, but are by no means limited to, fungal spores, mycelium, hyphae, and fragments of mycorrhizal infected roots. Experiments which have established the growth retarding activity of VA mycorrhizae are described below and illustrated in FIGS. 1 to 7 of the accompanying drawings.

Initial Experiments

Figure 1A:
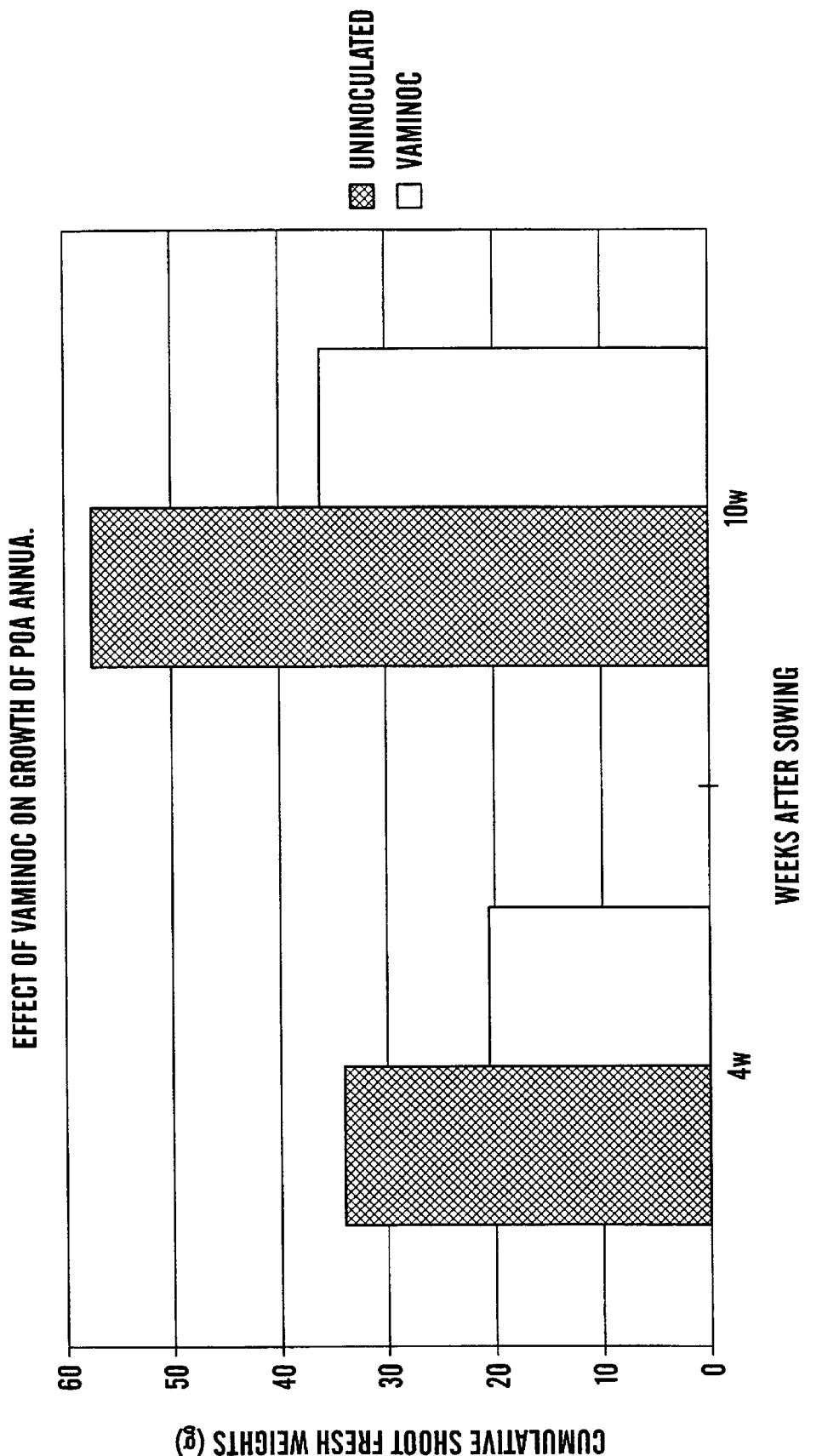
FIG. 1*a* graphically shows a significant reduction of growth of *Poa annua* in response to Vaminoc inoculation.

In July 1997, three soil cores, each 1.5 cm diameter were taken from all 18 greens on a golf course. Each core was examined under a binocular microscope and the number of tillers of each grass species counted. Roots of the grass species were then washed free of soil and placed on microscope slides. They were then examined under an epifluorescence microscope fitted with a UV bulb, under which conditions, the arbuscules (the only definitive structure of the mycorrhiza) autofluoresce. Mycorrhizae were quantified with the cross-hair eye piece method of McGonigle et al., 1990. Differences between greens in the abundance of AMG were tested for with Kruskall-Wallis one way Analysis of Variance and the relation between mycorrhizal colonisation and AMG abundance examined with linear regression.

Laboratory Experiment

Eighty flower pots, each measuring 7 cm×7 cm were filled with a mixture of 80% sand, 20% fen loam soil and sown with *Agrostis stolonifera* at the rate of 40 g m$^{-2}$. Half of the pots were inoculated with 8.7 g of Vaminoc-T, a four species mixture of mycorrhizal fungi (The MicroBio Group Ltd, Whittlesford, Cambridge, UK) equivalent to 25 g per liter of soil. Ten mycorrhizal and ten non-mycorrhizal pots then received 0.2 g of AMG (equivalent to 157,000 seeds m$^{-2}$), ten of each treatment received 0.4 g of AMG seed (314,000 seeds m$^{-2}$) and ten of each treatment, 0.6 g of AMG seed (471,000 seeds m$^2$). There were also ten pots of each mycorrhizal treatment which received no AMG seed. Therefore, in total there were eight treatments (2 levels of mycorrhiza×4 levels of AMG), with ten replicates of each, giving 80 pots.

Pots were maintained in a Constant Environment room at 20 C. for three months, by which time a close sward had developed. The cutting height of the grass was gradually reduced to 8 mm and at each cut the clippings were removed and dried to constant weight in an oven. Fertiliser was applied to mimic that recommended for an establishing green. At the end of the experiment the total biomass produced in each pot was calculated. The effect of adding AMG and the mycorrhiza on biomass production was analysed with a nested Analysis of Variance.

Results

There was an expected effect of AMG addition on total biomass, but no overall effect of mycorrhizal addition. However, there was a highly significant interaction between AMG and mycorrhiza ($F_{3,72}$=4.5, p<0.01). This was because when no AMG was added to the pots, addition of mycorrhiza increased the biomass of the bent grass. However, in all AMG addition treatments, the mycorrhiza did not increase the total biomass, and in some cases, significantly reduced it. These data therefore imply that mycorrhiza had a positive effect on the bentgrass, but a negative effect on the AMG. This can be seen by comparing pairs of treatments in the experiment. Thus, the addition of 0.2 g of AMG to non mycorrhizal pots caused an increase of 22% in total biomass, while the addition of 0.2 g of AMG to mycorrhizal pots resulted in a 3% decrease in biomass. Meanwhile adding 0.6 g of AMG to non-mycorrhizal pots gave a 45% increase, while adding 0.6 g of AMG to mycorrhizal pots gave only a 25% increase.

The results from the laboratory experiment lead to the following observations. In the 'control' situation, where no AMG was sown into the pots, the addition of mycorrhizae had a positive effect on the growth of the bentgrass. In pots where no mycorrhiza was added, then the addition of the AMG seed significantly increased biomass, as would be expected. However, if the mycorrhiza was present, addition of AMG at the level of 157,000 seeds m$^{-2}$ had no effect on the total biomass and actually resulted in a small decrease. Indeed even at the highest level of sowing (471,000 seeds m$^{-2}$), the mycorrhiza appeared to be able to mitigate the effects of this seed addition. The seed additions in this experiment were designed to be realistic compared with tiller densities in the field. The presence of mycorrhizal fungi may serve to maintain AMG at lower levels than would occur if the fungi were absent. Furthermore, this mechanism can work at tiller densities comparable to those encountered on courses.

Field Study

A significant negative relation between AMG abundance and mycorrhizal colonisation was again found ($F_{1,6}$= 8.65P<0.01, r$^2$=0.351). Mycorrhizal colonisation was very low, compared with natural areas, but was in the range (0–11%) The mean number of AMG tillers per core was 75.9+/_5.3.

*Agrostis stolonifera* in the course studied was virtually absent. In fact, 12 of the 18 greens appeared to be entirely AMG, and the mean AMG proportion in the sward was 96.1%. There was a significant difference between greens in the density of all crass tillers ($c^2=29.3$, $P<0.05$) and also in the proportion of AMG in the sward ($c^2=28.7$, $P<0.05$). Therefore, the greens were not providing uniform surfaces, due to the variable amounts of AMG in them.

Greenhouse Trials

Experiment 1

Effect of Vaminoc on Growth of *Poa annua*

8×1 liter trays, each measuring 20×15×5 cm were filled with 800 g of a mixture of sandy soil (kettering loam from Rothamsted Experimental Station) and sand (1:1 w/w). 4 trays each were inoculated with 0.7 g Vaminoc (equivalent to 20 g/m$^{-2}$), a three species mixture of VA-mycorrhizal fungi (MicroBio Group Ltd., Whittlesford, Cambridge, UK). and 4 trays were left uninoculated. VAM inoculation was performed by raking Vaminoc lightly into the soil surface before seed sowing. Each tray was sown with 1 g of *Poa annua* seeds, equivalent to the recommended rate of 35 g/m$^{-2}$, and maintained in a glasshouse at 25/20 ° C. day/night temperature.

Grass shoots were cut 4 and 10 weeks after sowing and Shoot Fresh Weight determined. At the end of the growth period (10 weeks) the total weights were calculated in each tray and root samples were stained and visually assessed for presence of VA-mycorrhizal colonization.

Figure 1B:
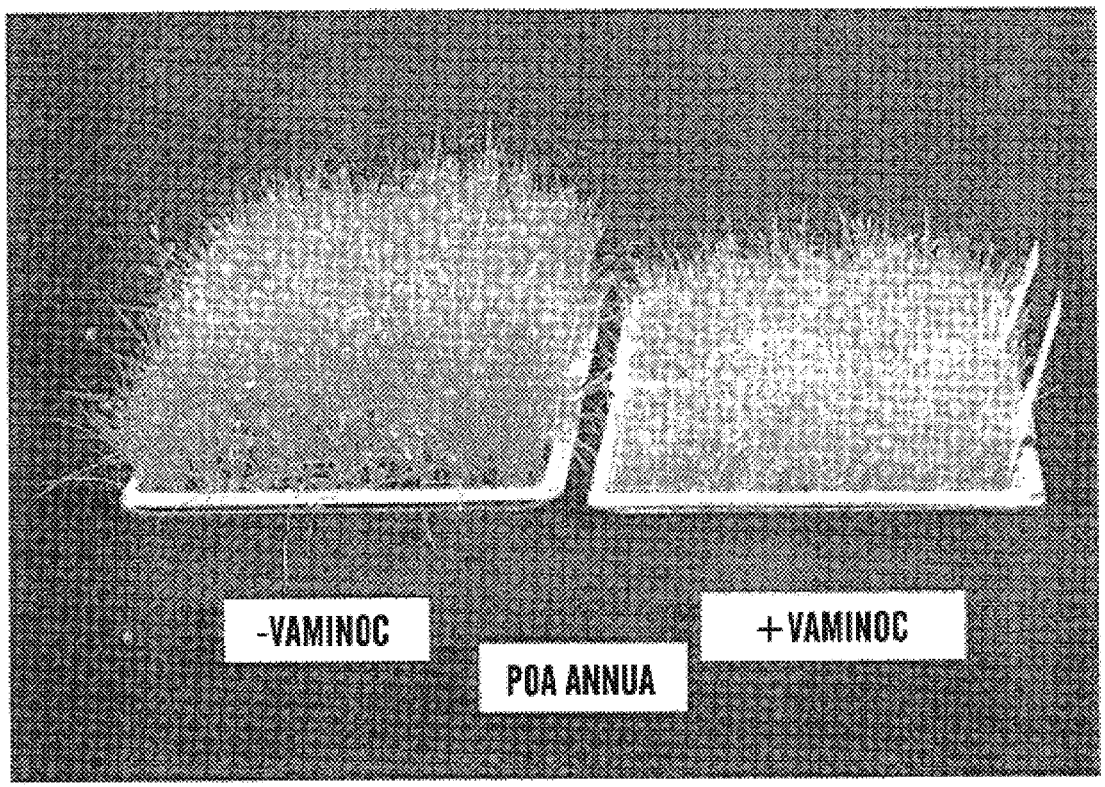
FIG. 1*b* photographically shows the detrimental effect of VA-mycorrhiza on Poa.

Results: FIG. 1*a* and FIG. 1*b* (photograph)

A significant reduction of growth of *Poa annua* in response to Vaminoc inoculation as compared to uninoculated controls was observed. The detrimental effect of VA-mycorrhizal on Poa can be seen in FIG. 1*b*, taken after 10 weeks growth, before 2nd fresh weight determination. VA-mycorrhizal colonization was present in inoculated Poa but not in uninoculated control.

Experiment 2

Effect of Vaminoc on *Poa annua* under three P levels

It is well established that the growth response of plants to mycorrhizal infection is influenced by the amount of phosphorus (P) supplied in the soil. When P is readily available to the plant the positive growth response due to mycorrhizal infection is also reduced, and it has been reported that high soil P levels reduce percentage infection in mycorrhizal plants.

Since VA-mycorrhiza have a negative effect on *Poa annua*, an experiment to study the relation between soil P levels and VAM response in Poa was performed by testing the effect of VAM inoculation under three P levels.

Materials and Methods were as indicated in Experiment 1.

Three soil P levels were chosen: no additional P(0), 152 g and 308 g of TripleSuperphosphate (TSP) per tray (equivalent to 0, 100, and 240 kg/ha respectively).

Therefore, there were 6 treatments (2 levels of mycorrhiza×3 TSP levels), with 4 replicates of each, giving a total of 24 trays.

Shoot fresh weight was determined in each tray 4 and 9 weeks after sowing. Total weights calculated after 9 weeks were analysed using a Two-way ANOVA.

Figure 2:
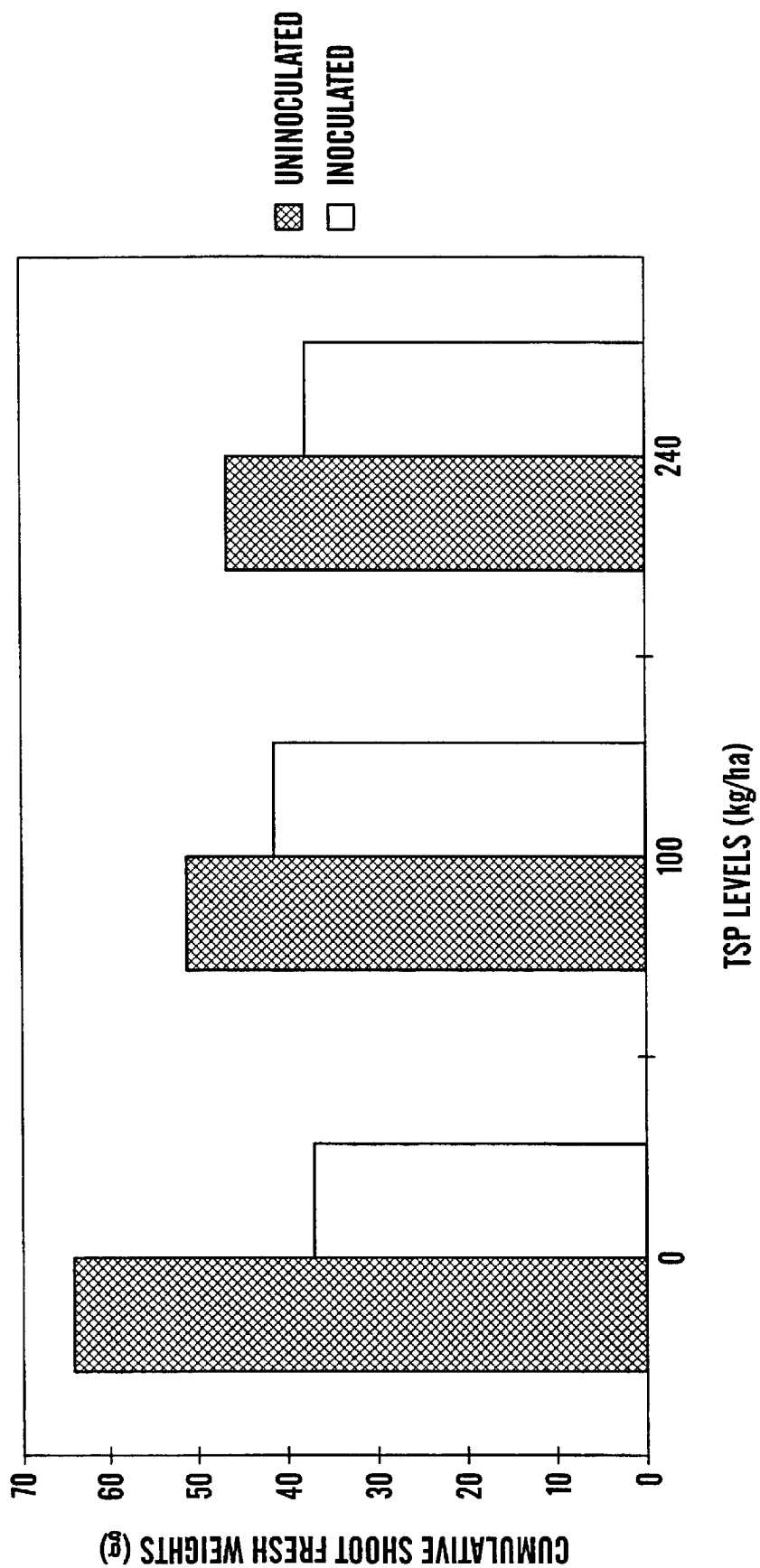
FIG. 2 shows that the weights for *Poa annua* trays not inoculated with Vaminoc were higher than those for the inoculated trays.

At the end of the experiment root samples were stained and checked for VAM fungal colonization. The results are shown in FIG. 2.

As expected, the overall weights for *Poa annua* trays not inoculated with Vaminoc were higher than those for the inoculated trays ($F_{1,18}=57.37; p<0.01$). There was also a difference in the overall weights for the different levels of TSP ($F_{2,18}=5.97; p=0.01$).

Growth responses of Poa to the three TSP levels were different in inoculated as compared to uninoculated trays ($F_{2,18}=8.87; p=0.002$). In inoculated trays the growth retardant effect of Vaminoc was observed at all P levels tested.

At the end of the experiment. VAM colonization in roots of all inoculated Poa treatments were observed as compared to no colonization in the uninoculated controls. Some mycorrhizal fungi are detrimentally affected by high soil phosphorus levels. When soil phosphorus is abundant, some fungal species grow very poorly and plant response is also reduced. However, an important feature of the effect described above is that the antagonistic effect on *Poa annua* has been found at low, medium and high soil P levels. The 'high' P level in this experiment corresponded to that found in typical putting green soil, where levels are invariably high. Thus, the antagonistic effect of the fungi on *P. annua* occurs in realistic situations, such as those found in golf greens.

EXAMPLE 1

A practice putting green was used for the experiment. This was composed of a mixture of Agrostis spp. and *Poa annua*, with small amounts of Festuca spp. The experiment took 6–7 months from late June onward. Twenty four plots, each 0.5 m×0.5 m were laid out on the green and each plot was subjected to one of four treatments:

Addition of Agrostis seed, as an overseed, @4 g per plot

Addition of Vaminoc-T, @5 g per plot

Addition of seed and inoculum

Addition of neither ('control').

The plots were arranged randomly on the green, with six replicates of each treatment. Grass abundance was sampled non-destructively by the point quadrant method. Twenty 3 mm diameter metal pins were placed randomly in each plot, so that the tip of each pin rested on the soil surface. The total number of touches of each crass species on each pin was counted, and summed over the 20 pins in each plot. Plots were sampled on five occasions over a six month period after the treatments had been applied. The average value was then calculated across the six replicates for each treatment on each date. The averages are displayed in the accompanying figures.

Figure 3:
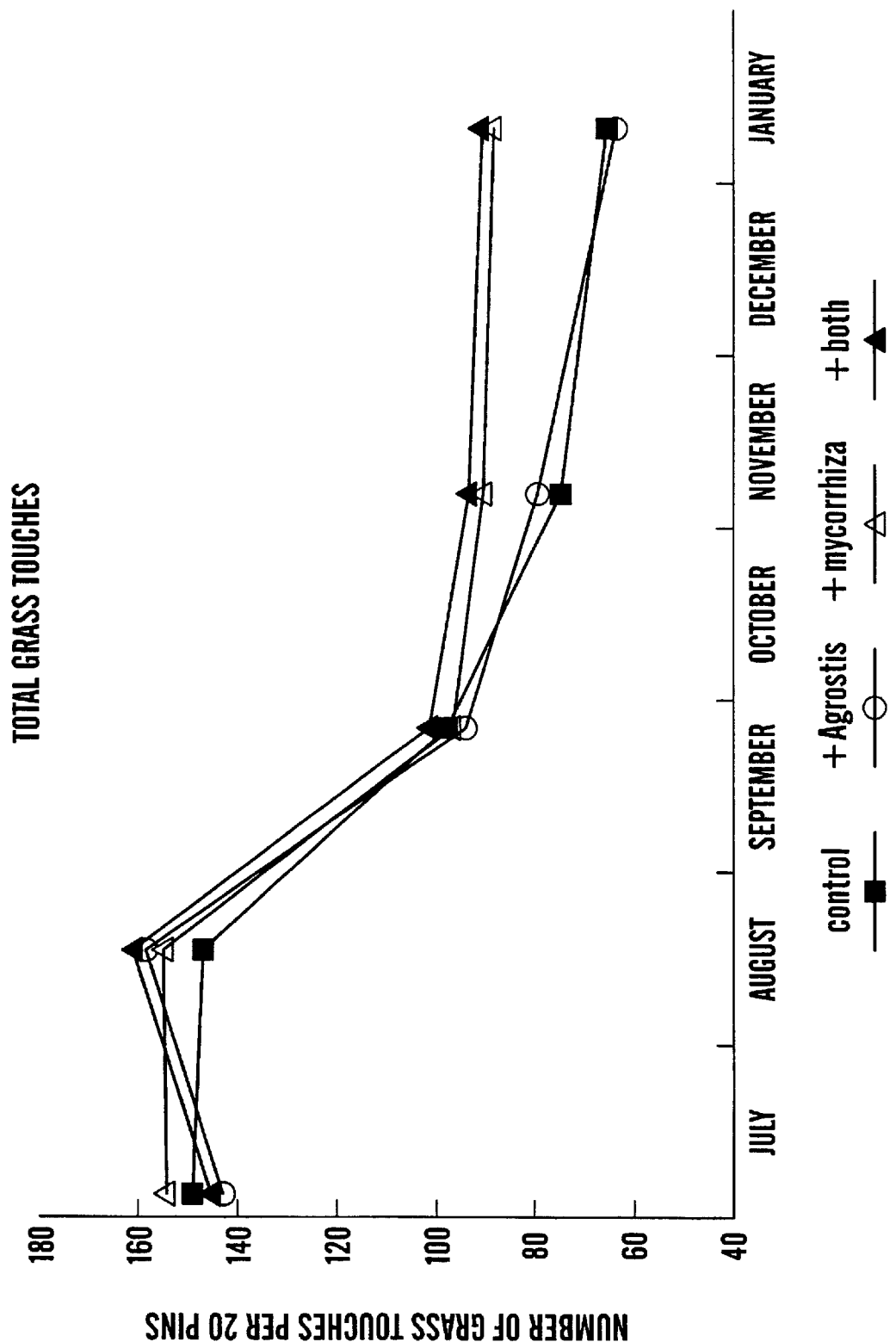
FIG. 3 shows that grass treated with the Vaminoc-T mycorrhiza inoculant had significantly more total grass touches.
Figure 4:
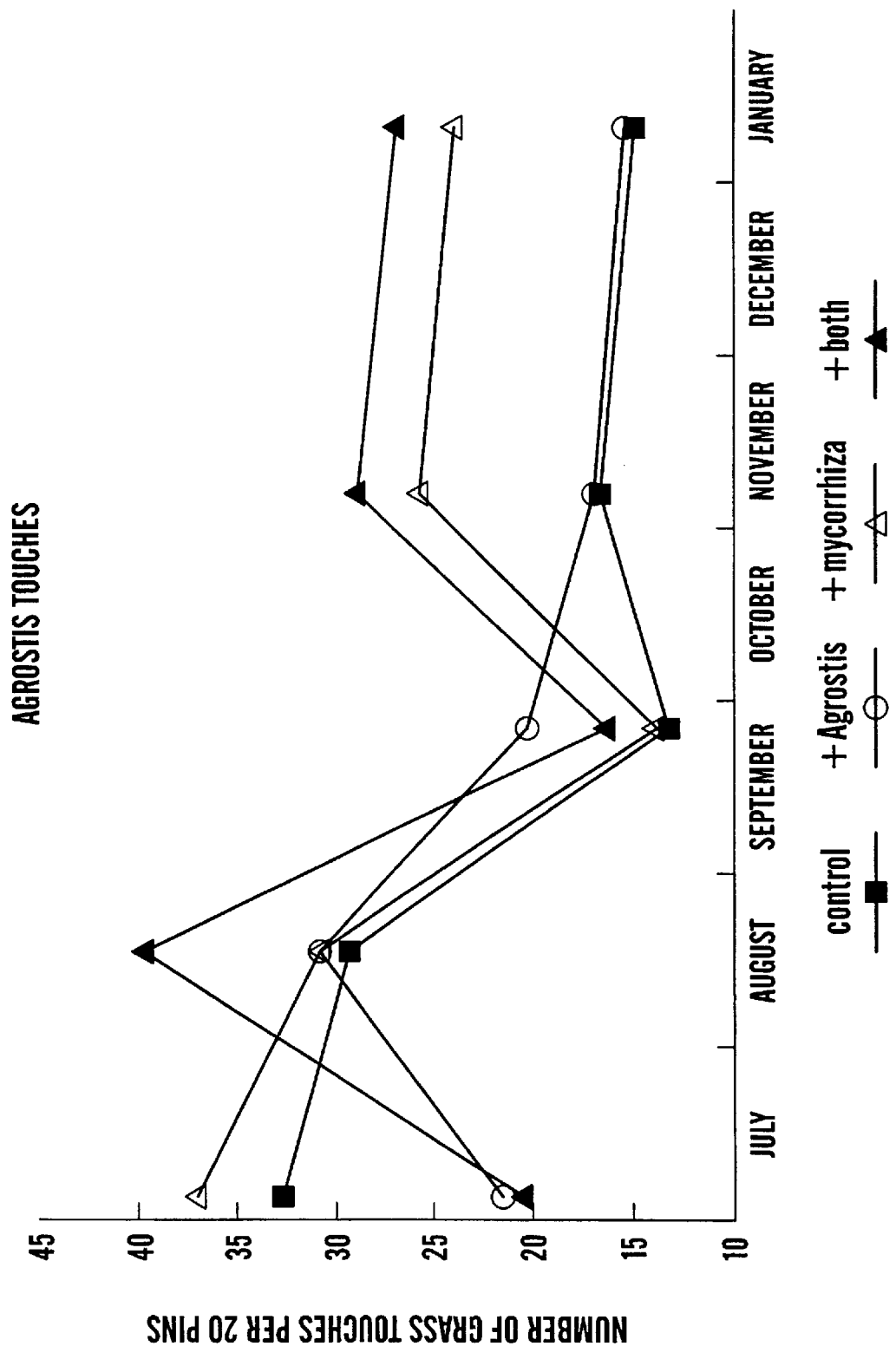
FIG. 4 shows that grass treated with Vaminoc-T had more touches of Agrostis.
Figure 5:
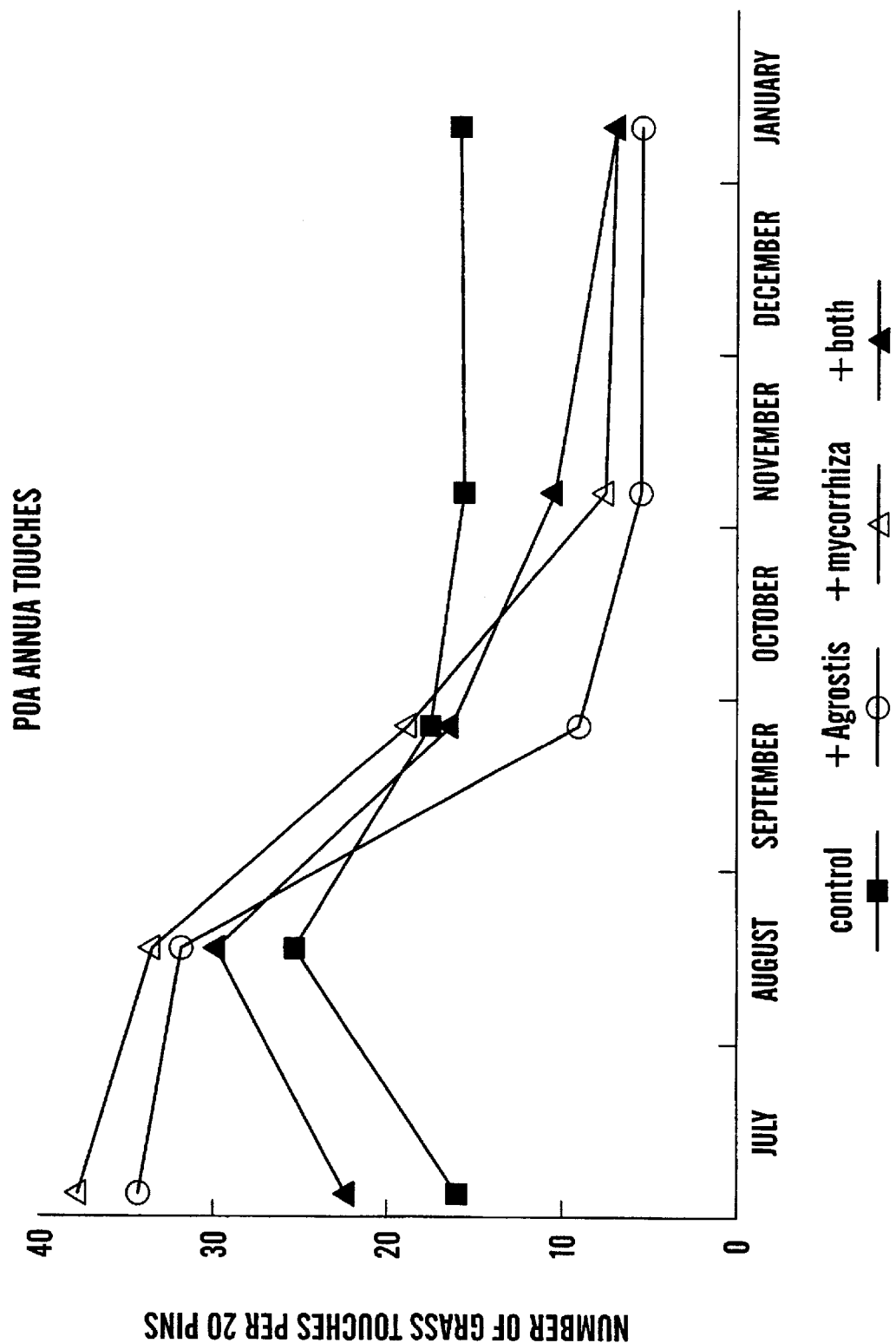
FIG. 5 shows that plots treated with Vaminoc-T had fewer touches of *Poa annua* than the controls.

Results (see FIGS. 3, 4, and 5)

At the start of the experiment, the total amount of grass in each treatment was similar. Addition of seed had no effect on the total amount of grass, or that of the two commonest species, Agrostis and Poa. However, by the end of the study, treatments which had the Vaminoc-T mycorrhiza inoculant applied to them had significantly more total grass touches (FIG. 3). The addition of the fungi therefore had stimulatory effect on sward growth with more grass blades being touched by the 20 pins. However, the effect on the two dominant grass species was not the same. The treatments in which Vaminoc-T was applied had more touches of Agrostis at the end of the six-month period, as shown by the lines marked with triangles in FIG. 4. Therefore, the fungi were much more effective in increasing abundance of this grass than was the addition of seed.

Meanwhile, at the end of the experiment, plots which received Vaminoc-T had fewer touches of *Poa annua* than did the plots in which no treatment was applied (FIG. 5). This was a complete reverse of the situation at the start of the experiment, when 'control' plots had the lowest Poa count.

Therefore, application of Vaminoc-T to a working golf green resulted in a reduction in *Poa annua* abundance, an increase in Agrostis abundance and an increase in overall grass abundance.

EXAMPLE 2

VAM Field Efficacy

For the purpose of this demonstration, two US PGA constructed greens were selected from a large popular golf course in Cambridgeshire-UK. The greens were seeded approximately three years previous, and managed as per standard practice. Much of the green was composed of Agrostis spp., with a low level of Festuca spp. *Poa annua* was evident across much of the two selected greens.

Each 500 m² green was split equally into two plots. The greens were hollow-tined prior to treatment. Vaminoc-G was applied at 20g m² to one half of each green, whilst the other half remained untreated. Each green was lightly irrigated within 8 hours of Vaminoc-G application.

Each green was visually assessed for *P. annua* incidence prior to Vaminoc-G application, and again approximately 2 months after application.

Greens were managed as standard practice during the course of the trial.

Results

Figure 6:
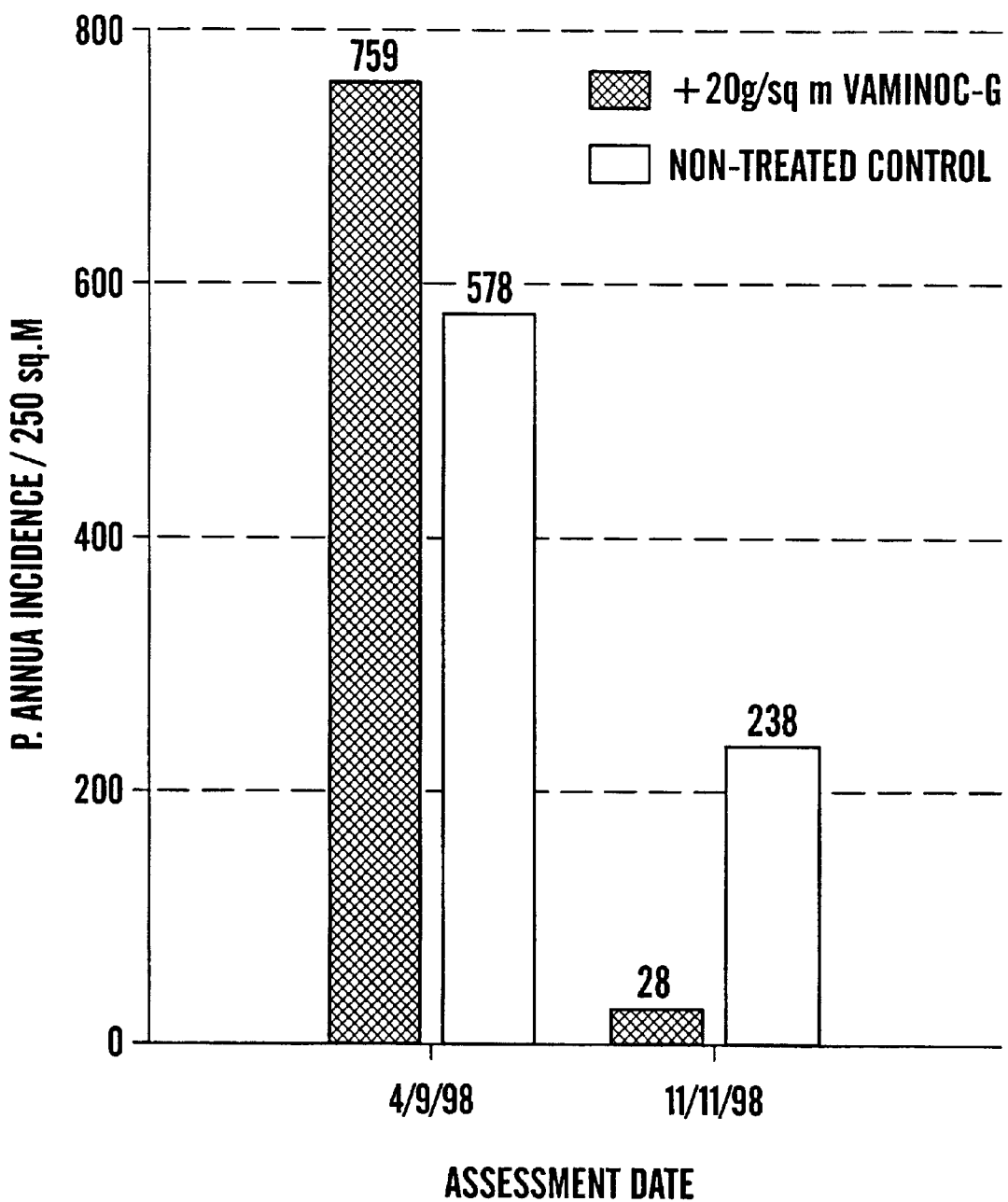
FIGS. 6 and 7 show the relationship between Vaminoc-G application and incidence of *Poa annua* on golf greens.
Figure 7:
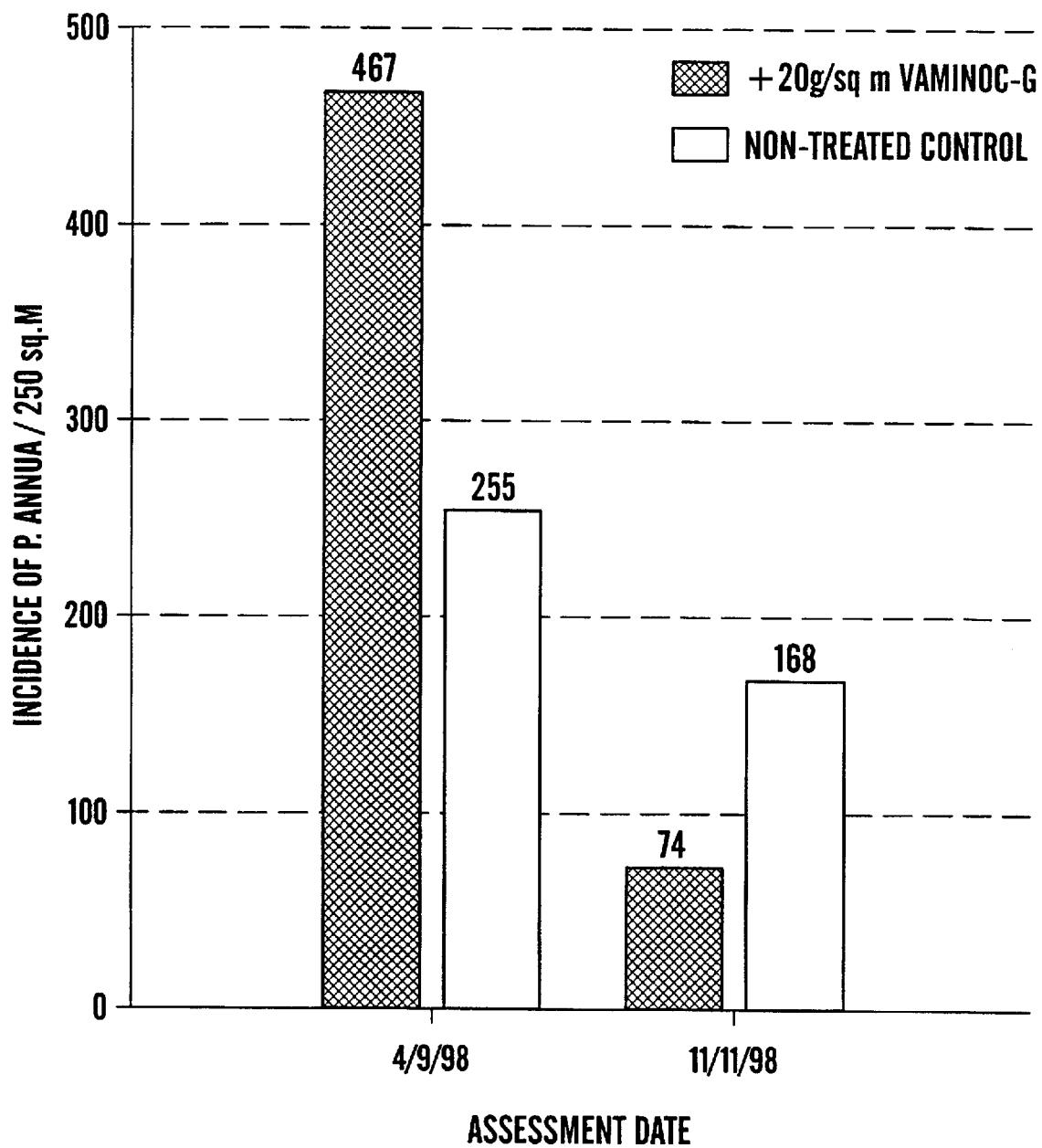

The relationship between Vaminoc-G application and incidence of Poa annua for both greens are recorded on the accompanying FIGS. 6 and 7. It is evident that although the incidence of *P. annua* generally declines in the greens over the assessment period as expected, the total percentage reduction in the Vaminoc-G treatment areas is far higher than that recorded in the non-treated areas (96% and 84% cf. 59% and 34% for green 1 and 18 respectively).

What is claimed is:

1. A method of retarding growth of *Poa annua* in grass containing at least a small amount of *Poa annua*, the method comprising applying VA mycorrhiza to the grass.

2. The method of claim 1 using one or more strains of VA mycorrhiza selected from genera Glomus, Acaulospora, Entrophosphora, Gigaspora, Scutellospora and Sclerocytis.

3. The method of claim 1 using one or more strains of VA mycorrhiza selected from the group consisting of *Glomus fasciculatum, Glomus caledonium, Glomus mosseae, Glomus versiforme, Glomus intraradices* and *Glomus etunicatum*.

4. The method of claim 1 wherein the grass is turfgrass.

5. The method of claim 4 wherein the turfgrass is one of
 a. a golfing green, or
 b. an amenity turf.

6. The method of claim 4 wherein the major portion of the turfgrass is formed of at least one of Agrostis Spp. and/or Festuca Spp.

7. A method of controlling or reducing the growth of *Poa annua* in turfgrass which comprises applying to the turfgrass infective propagules of one or more strains of VA mycorrhiza which are growth-controlling for *Poa annua*.

8. The method of claim 7 wherein the infective propagules are selected from fungal spores, mycelium, hyphae, and fragments of mycorrhiza infected roots.

9. The method of claim 7 wherein the one or more strains of VA mycorrhiza are selected from genera Glomus, Acaulospora, Entrophosphora, Gigaspora, Scutellospora and Sclerocytis.

10. The method of claim 7 wherein the one or more strains of VA mycorrhiza are selected from the group consisting of *Glomus fasciculatum, Glomus caledonium, Glomus mosseae, Glomus versiforme, Glomus intraradices* and *Glomus etunicatum*.

11. The method of claim 7 wherein the infective propagules are formulated with a substantially chemically inert solid carrier.

12. The method of claim 11 wherein the solid carrier contains at least one of clay, silica gel, bleaching earths, pumice, bauxite, attapulgite, vermiculite, calcined montmorillinite, soil, peat, or sand.

13. The method of claim 7 wherein the infective propagules are applied to the turfgrass as a part of a formulated product wherein the propagules constitute the principal component having biological activity on the growth of turfgrass.

14. The method of claim 13 wherein the formulated product has an MPN of from about 200 to 1000 or more propagules per gram.

15. The method of claim 13 wherein the amount of formulated product applied to the turfgrass is from about 5 g/m2 to about 1 kg/m2.

16. A method for the control of the growth of *Poa annua* in grass comprising applying to the grass a composition which contains one or more strains of VA mycorrhiza and is substantially free from any biological agent having direct or indirect *Poa annua* growth-promoting activity.

17. The method of claim 16 wherein the one or more strains of VA mycorrhiza are selected from genera Glomus, Acaulospora, Entrophosphora, Gigaspora, Scutellospora and Sclerocytis.

18. The method of claim 16 wherein the one or more strains of VA mycorrhiza are selected from the group consisting of *Glomus fasciculatum, Glomus caledonium, Glomus mosseae, Glomus versiforme, Glomus intraradices* and *Glomus etunicatum*.

19. The method of claim 16 wherein the composition contains a solid carrier chosen from at least one of clay, silica gel, bleaching earths, pumice, bauxite, attapulgite, vermiculite, calcined montmorillinite, soil, peat, or sand.

* * * * *